United States Patent
Zhou et al.

(10) Patent No.: US 10,159,832 B2
(45) Date of Patent: Dec. 25, 2018

(54) ELECTRODE WITH INCREASED STABILITY AND METHOD OF MANUFACTURING THE SAME

(75) Inventors: Dao Min Zhou, Saugus, CA (US); Jerry Ok, Canyon Country, CA (US); Neil Hamilton Talbot, La Crescenta, CA (US); Brian V. Mech, Stevenson Ranch, CA (US); James Singleton Little, Saugus, CA (US); Robert J. Greenberg, Los Angeles, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 1273 days.

(21) Appl. No.: 11/924,763

(22) Filed: Oct. 26, 2007

(65) Prior Publication Data
US 2008/0268134 A1 Oct. 30, 2008

Related U.S. Application Data

(62) Division of application No. 11/820,744, filed on Jun. 19, 2007.

(60) Provisional application No. 60/814,976, filed on Jun. 19, 2006, provisional application No. 60/815,037, filed on Jun. 19, 2006.

(51) Int. Cl.
*C25D 5/02* (2006.01)
*A61N 1/05* (2006.01)
*A61N 1/36* (2006.01)

(52) U.S. Cl.
CPC ........ *A61N 1/0543* (2013.01); *A61N 1/36046* (2013.01)

(58) Field of Classification Search
USPC ........................................... 205/118, 122, 186
See application file for complete search history.

(56) References Cited

U.S. PATENT DOCUMENTS

| | | | |
|---|---|---|---|
| 5,109,844 A | 5/1992 | de Juan, Jr. et al. | |
| 5,476,494 A * | 12/1995 | Edell et al. | ........... 607/116 |
| 5,935,155 A | 8/1999 | Humayun et al. | |
| 6,400,989 B1 | 6/2002 | Eckmiller | |
| 6,458,157 B1 | 10/2002 | Suaning | |

(Continued)

FOREIGN PATENT DOCUMENTS

| | | |
|---|---|---|
| EP | 0 442 674 A2 | 8/1991 |
| WO | WO 2007/058975 A2 | 5/2007 |

OTHER PUBLICATIONS

Maghribi, M., et al. "Stretchable Micro-Electrode Array," 2nd Annual INternational IEE-EMBS Special Topic Conference on Microtechnologies in Medicine & Biology, May 2-4, 2022, IEEE.*

(Continued)

*Primary Examiner* — Stefanie S Wittenberg
(74) *Attorney, Agent, or Firm* — Scott Dunbar (57) ABSTRACT

The present invention provides an implantable electrode with increased stability wherein the surface is of the electrode comprises mesh grids which are filled with sticks which are filed with a conducting or insulating material. The present invention further provides a method of manufacturing an electrode with increased stability, comprising: depositing a metal layer on an base layer; applying photoresist layer on the metal layer; patterning the photoresist layer providing openings; electroplating the openings with metal; removing the photoresist layer leaving spaces; and filling the spaces with polymer.

8 Claims, 6 Drawing Sheets

(56) References Cited

U.S. PATENT DOCUMENTS

| | | |
|---|---|---|
| 6,974,533 B2 | 12/2005 | Zhou |
| 2002/0158342 A1 | 10/2002 | Tuominen et al. |
| 2003/0195601 A1* | 10/2003 | Hung et al. .................. 607/116 |

OTHER PUBLICATIONS

Kwon, Gu-Han., et al. "Fabrication and Evaluation of the Flexible and Implantable Soft Micro Electrode for Retinal Prosthesis," Proceedings of 2006 International Conference on Microtechnologies in Medicine and Biology, Japan May 9-12, 2006, IEEE.*

M. Maghribi, et al.; Stretchable Micro-Electrode Array; 2nd Annual Int. IEEE-EMBS Special Topic Conf. on Microtechnologies in Medicine & Biology, May 2-4, 2002, Madison, WI.

Oded Rabin, et al.; Formation of Thick Porous Anodic Alumina Films and Nanowire Arrays on Silicon Wafers and Glass; Advance Functional Materials; 2003, 13, No. 8, Aug.

* cited by examiner

ELECTRODE WITH INCREASED STABILITY AND METHOD OF MANUFACTURING THE SAME

CROSS REFERENCE TO RELATED APPLICATIONS

This application is a divisional of application Ser. No. 11/820,744, entitled "Electrode with Increased Stability and Method of Manufacturing the Same", filed Jun. 19, 2007, which application claims priority to provisional Application No. 60/814,976 for "Method to Increase Electrode's Stability" filed on Jun. 19, 2006, and to U.S. Provisional Application No. 60/815,037 for "New Electrode Design" filed on Jun. 19, 2006, which are both incorporated herein by reference in their entirety.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to an electrode with increased stability and method of manufacturing the same. In particular the present invention is directed to a new electrode design.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatus to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

US Patent Application 2003/0109903 to Berrang describes a Low profile subcutaneous enclosure, in particular and metal over ceramic hermetic package for implantation under the skin.

Current on electrode surfaces tends to flow mainly from the edge of the metal surface. This is called edge effect for stimulating electrodes. Edge effect can cause tissue damage due to uneven current distribution. This effect can be minimized for a given electrode by increasing the edge.

Thin film techniques may not provide enough electrode materials on the electrode surface for chronic stimulation. Further, common electroplating technique presents stress problem that limits the plated layer to less than 1 µm.

SUMMARY OF THE INVENTION

The present invention is generally directed to an electrode with increased stability and method of manufacturing the same. In particular the present invention is directed to a new electrode design.

The present invention provides electrode designs and methods for manufacturing electrodes with higher stability and improved adhesion of the electrode material on the substrate.

One aspect of the present invention is an electrode array containing electrodes with different shapes.

Another aspect of the present invention are electrodes with a clustered surface. The surface of an electrode is covered with an insulated material and openings are provided in the area of the electrode into the insulating material resulting in a cluster.

Another aspect of the present invention are electrodes containing a grid on the surface comprising at least one metal and/at least one polymer.

Another aspect of the invention is that the openings have different shapes.

Another aspect of the present invention is a method of manufacturing an electrode with increased stability, comprising:
a) depositing a metal layer on an base layer;
b) applying photoresist layer on the metal layer;
c) patterning the photoresist layer providing openings;
d) electroplating the openings with metal;
e) removing the photoresist layer leaving spaces; and
f) filling the spaces with polymer.

Another aspect of the present invention is a method of manufacturing an electrode with increased stability, comprising:
a) depositing a metal layer on an base layer;
b) applying a polymer layer on the metal layer;
b) applying photoresist layer on the polymer layer;
c) patterning the photoresist layer providing openings;
d) electroplating the openings with metal; and
e) removing the photoresist layer.

DETAILED DESCRIPTION OF THE INVENTION

The present invention is generally directed to an electrode with increased stability and method of manufacturing the same. In particular the present invention is directed to a new electrode design. The present invention provides an electrode for an implantable electrode array with an improved current distribution and adhesion for neural stimulation electrodes.

Sputtered thin film electrodes may not provide enough electrode material on the electrode array surface for chronic stimulation. The electrodes are too thin and smooth and dissolve easily. Electroplating adds more material to increase the life time of the electrode. The electrodes are thicker and more solid. However, high stress problems, such as cracking or delaminating, limit the plating thickness to <1 µm which is the thickness normal dense plating.

According to the method of the present invention electrodes (Pt, Ir, Pd, IrO) were electroplated with a diameter of 50 µm-500 µm and a thickness of 2 µm-3 µm on a substrate, such as a polymer, like polyimide, silicone, peek or parylene, or mixtures thereof.

One aspect of the invention is to provide a mesh or grid of a different metal, such as Ti, Zr, Ta or mixtures or alloys thereof, or a polymer, such as silicone, polyimide, peek or parylene or mixtures thereof. The mesh or grid has a height of 5 µm-35 µm, preferably 22 µm-27 µm.

Another aspect of the invention includes an additional electroplating step on top of the mesh or grid. In this case an embedded mesh or grid can be obtained.

Another aspect of the invention is to plate micro sticks with a dense structure on sputtered electrode surface as a support. As next step a porous and loose layer with low stress is applied on top of the electrode to cover the electrode surface.

Figure 1:
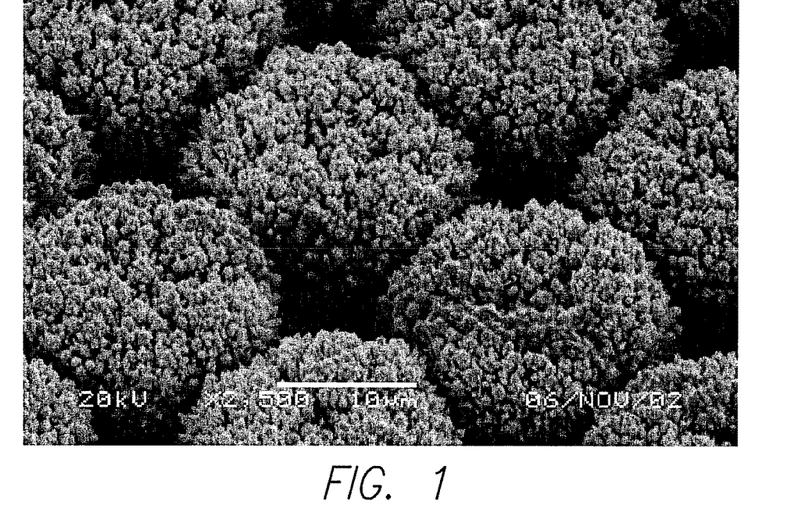
FIG. 1 depicts a SEM imaging (×2,500) of electroplated platinum filled with grids of insulation polymers.

FIG. 1 depicts a SEM imaging (×2,500) of electroplated platinum filled with grids of insulation polymers. The electrode of platinum containing the grid of polymer can be produced according to the process shown in FIG. 3. By adding insulated lines on the metal surface more edges are created. An increase of the edges minimizes the edge effect or electrical discharge. For example, an electrode surface has a metal disk with a diameter of d, the edge length is π*d. If an insulated cross is added on the metal surface, the edge length is increased from π*d to (4d+π*d), which is over 120% increase in edge length. For a square metal surface, it has a 100% increase from 4d to 8d.

In thin-film electrodes added insulation lines also serve as a protector for the metal layer to hold it from delaminating.

In thick-film electrodes, a cut on the electrode surface will provide similar effect as an insulated line. The impedance is much higher inside the cut due to lower conductivity of electrolyte, which will force current flow through the edge of the cut.

Figure 2:
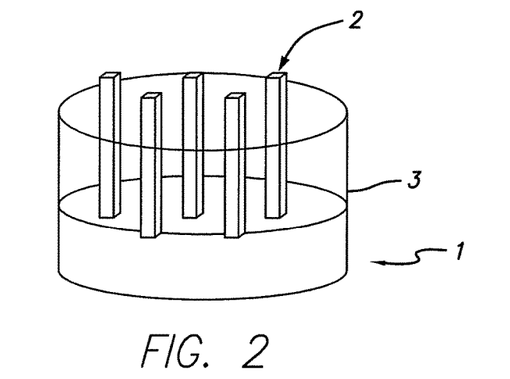
FIG. 2 depicts a spherical view of an electrode with micro sticks/posts.
Figure 3A:
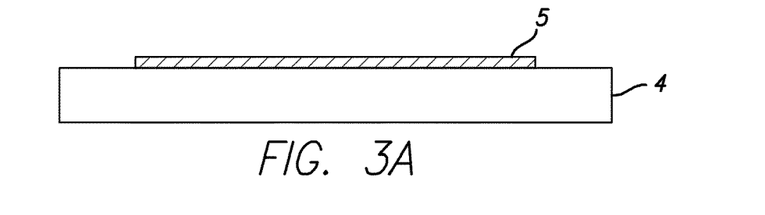
FIG. 3A-FIG. 3F depict a process scheme for manufacturing electroplated sticks/posts and polymer filling.
Figure 3B:
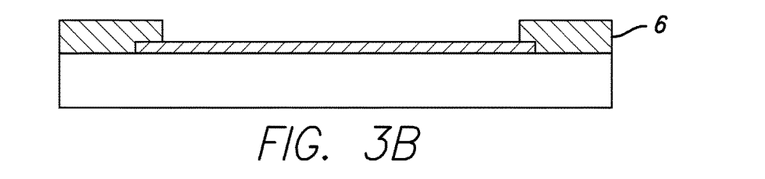
Figure 3C:
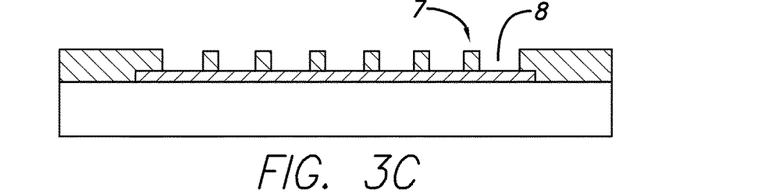
Figure 3D:
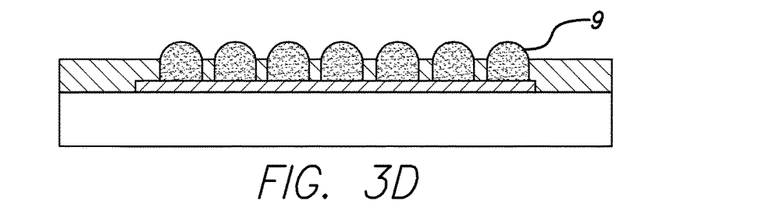
Figure 3E:
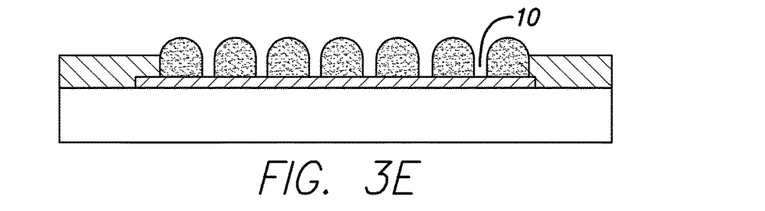
Figure 3F:
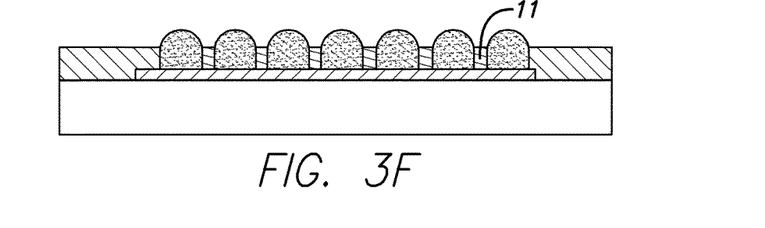

FIG. 2 depicts a spherical view of an electrode with micro sticks/posts. First a sputtered metal layer 1 is provided, then micro stick/post 2 are produced and finally the gabs are filled in by polymer such as PDMS or epoxy wherein a plated soft low stress layer 3 is provide. The process is shown in FIGS. 3A-3F and in FIGS. 5A-5C.

Thin-film techniques can't provide enough electrode materials on the electrode surface for chronic stimulation. By electroplating a layer of electrode material on sputtered metal layer increases array's life time to several folds. However, normal electroplating technique presents stress problem that limited the plated layer to <1 μm. 2-3 μm thick of metal layer is successfully plated on thin-film Pt electrode with disk opening up to 500 μm. Micro sticks of Au and Pt can be plated up to 25 μm. There are several methods to reduce stress in plated metal layer according to the present invention which include:
1. Optimizing plating conditions to increase plated layer to 4-5 μm: surface pre-treatment (include cleaning or surface modification, redox status), surfactant, solution concentration, complex compounds, temperature, pH, stirring, current or voltage control (amplitude, waveform and frequency), or gas purge.
2. Plating micro sticks with dense structure on the electrode surface as support structure, then plate a porous and loose layer with low stress to cover the electrode surface.
3. Plating 2-3 μm thick of metal layer, then sputtering a mesh (or grid) of Ti to fix or hold the plated layer. Repeating above step until desired thickness (layer) is obtained. Each plated layer will be softer than the layer below. Top layer can be a porous material such as Pt black.
4. Add grids of polyimide on sputtered Pt surface. Then plate soft Pt on sputtered surface. The polyimide grids will separate or isolate plated surface and reduce stress.

Materials for sticks can be same as or different from plated surface layer. For example, stick is dense Pt and plated layer is Pt black; or stick is Pt and plated layer is IrOx; support mesh grid can be metal or polymer, such as Ti or polyimide. The metal for electroplating the posts can be Pt, Ir, Au, Ru, Pd, or alloys thereof.

Figure 4A:
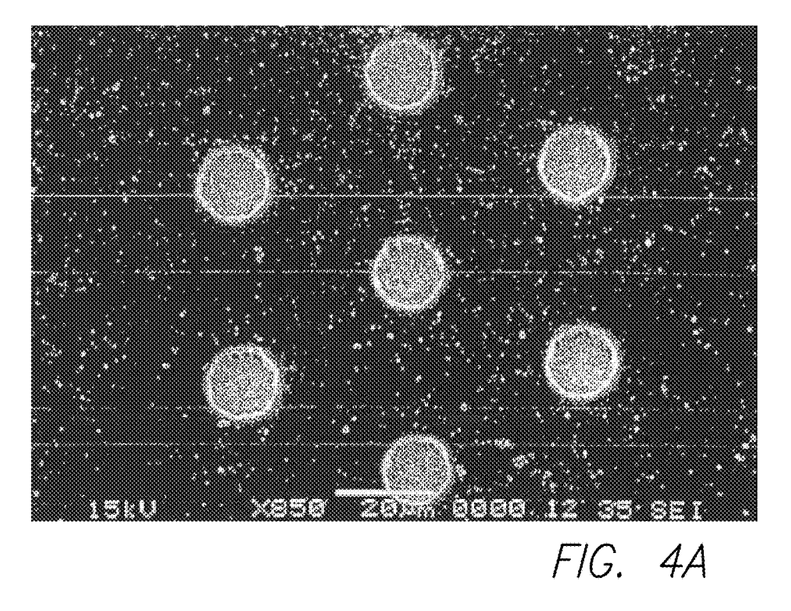
FIG. 4A depicts a SEM imaging (×850) of polymer surface with patterned holes before Pt plating.

FIG. 3 depicts a process scheme for manufacturing electroplated sticks/posts 3 and polymer filling 2. In particularly six steps of the process are shown. In step I a thin film 5 of Pt, Ir, Au, Ru, Pd, or alloys thereof is applied by sputtering on a substrate 4. In step II a polymer 6 covering the edge of the electrode is applied. In step III a photoresist layer 7 is applied and a patterning by MEMS is performed whereby holes 8 are created. The holes 8 are filled with electroplated metal 9 like Pt in step IV. In step V the photoresist 7 is removed leaving spaces 10 between the metal sticks or posts 9. The spaces 10 between the sticks are filled with polymer 11 adhesive such as PDMS or epoxy in step VI. The obtained electrode is the electrode shown in FIG. 2 with micro stocks FIG. 4A depicts a SEM imaging (×850) of polymer surface with patterned holes 8 before Pt plating 9 as shown in step III.

Figure 4B:
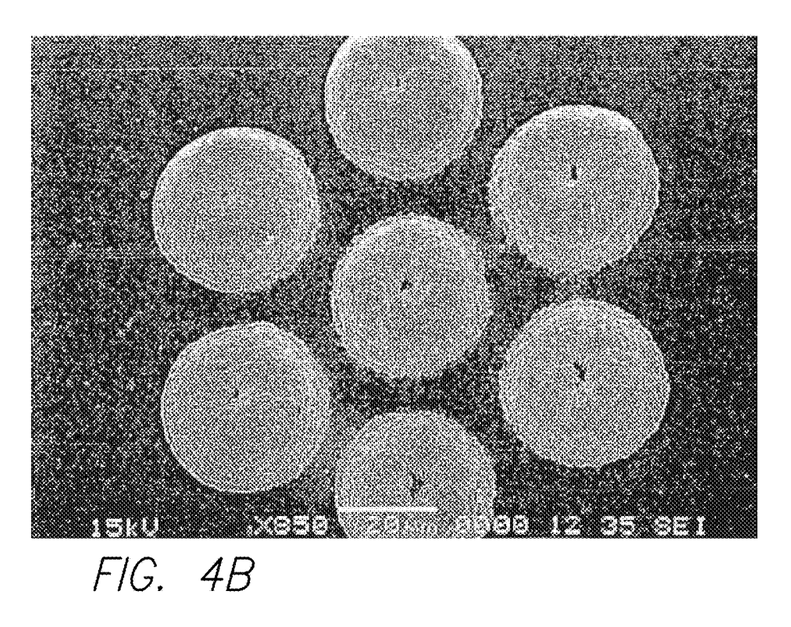
FIG. 4B depicts a SEM imaging (×850) of polymer surface with patterned holes after Pt plating.

FIG. 4B depicts a SEM imaging (×850) of polymer surface with patterned holes after Pt plating 9 as shown in step IV.

Figure 5A:
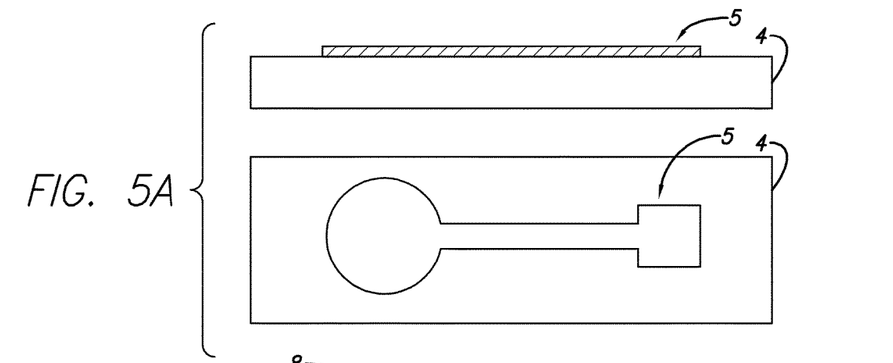
FIG. 5A-FIG. 5C depict a process scheme for manufacturing electroplated sticks/posts and polymer filling.
Figure 5B:
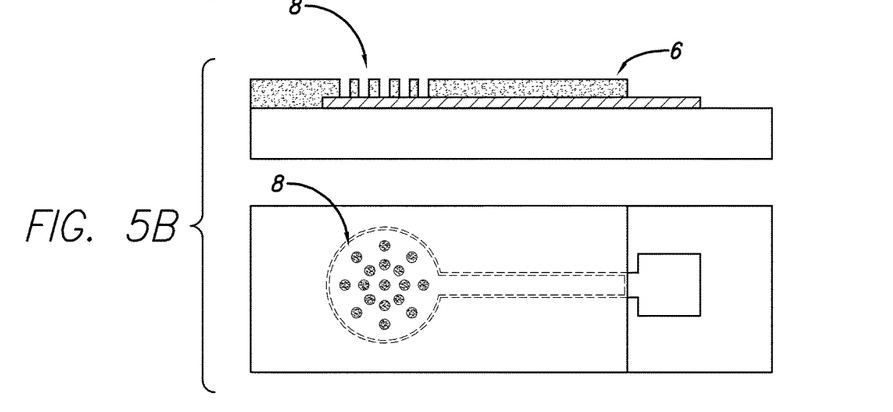
Figure 5C:
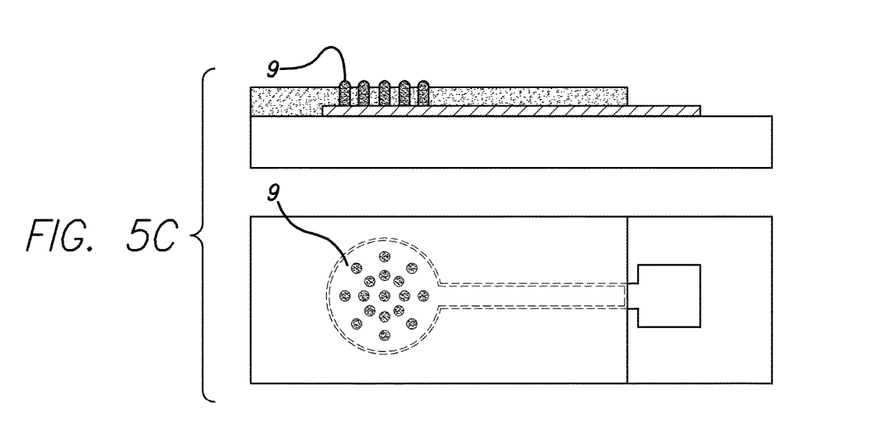

FIG. 5A-FIG. 5C depict a process scheme for manufacturing electroplated sticks/posts 3 and polymer filling 2. In particularly three steps of the process are shown. In step I to be seen as cross sectional view and top view a thin film 5 of Pt, Ir, Au, Ru, Pd, or alloys thereof is applied by sputtering on a substrate 4. In step II a polymer 6 covering the edge of the electrode is applied and is patterned whereby holes 8 are created. The holes 8 are filled with electroplated metal 9 like Pt in step III. The obtained electrode is the electrode shown in FIG. 2 with micro sticks 3 and polymer 6 in the spaces.

Figure 6:
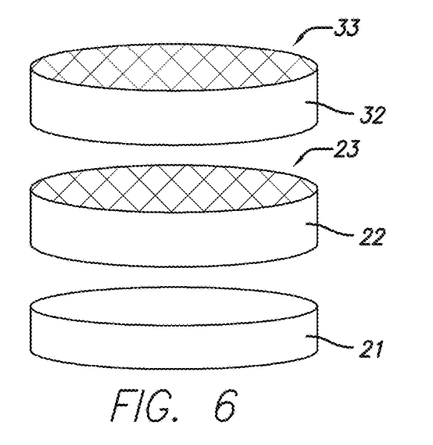
FIG. 6 depicts a spherical view of an electrode with mesh grid as fixture.

FIG. 6 depicts a spherical view of an electrode with mesh grid as fixture. First a sputtered metal layer 21 is provided, then a low stress layer 22 is plated and a grid is obtained and filled with a polymer like polyimide, silicone, peek or parylene, or mixtures thereof or metal Pt, Ir, Au, Ru, Pd, or alloys thereof to create a mesh grid 23. The steps can be repeated to apply a second low stress layer 32 which is plated and a grid is obtained and filled with a polymer like polyimide, silicone, peek or parylene, or mixtures thereof or metal Pt, Ir, Au, Ru, Pd, or alloys thereof to create a mesh grid 33 are produced and finally the gabs are filled in by polymer such as PDMS or epoxy wherein a plated soft low stress layer 3 is provide. The process is shown in FIGS. 3A-3F and in FIGS. 5A-5C.

Figure 7:
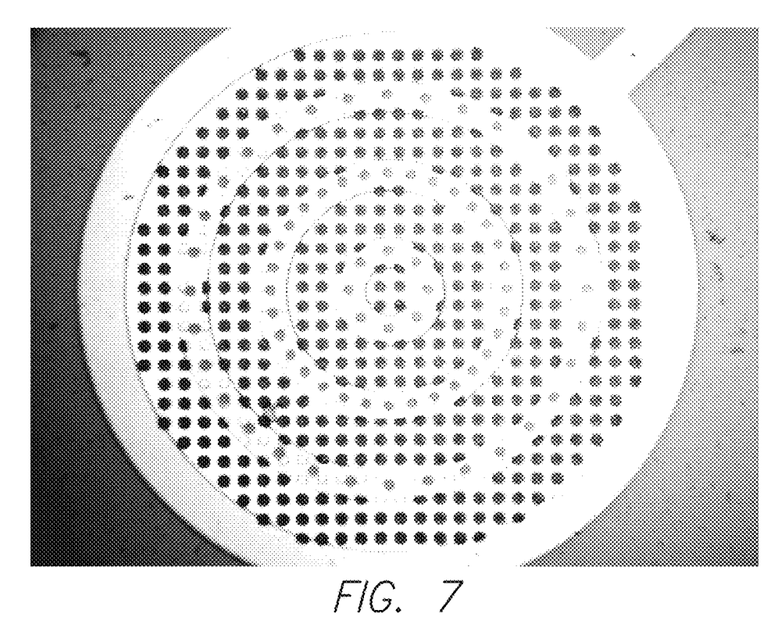
FIG. 7 depicts an electrode with polymer rings as fixture.

FIG. 7 depicts an electrode with polymer rings as fixture. This is an alternative to the mesh grid as shown in FIG. 6. The rings can be polymer rings or exposed metal. A multi-ring electrode is achieved by selectively insulating a conductive pad in an appropriate pattern concentric ring such as to leave exposed concentric rings of metal in between successively larger isolation rings. Novel design feature are small circles radial patterned in the metal pad exposing the substrate material. These circles serve as anchor points for the adhesion of the insulation rings to the substrate.

Figure 8:
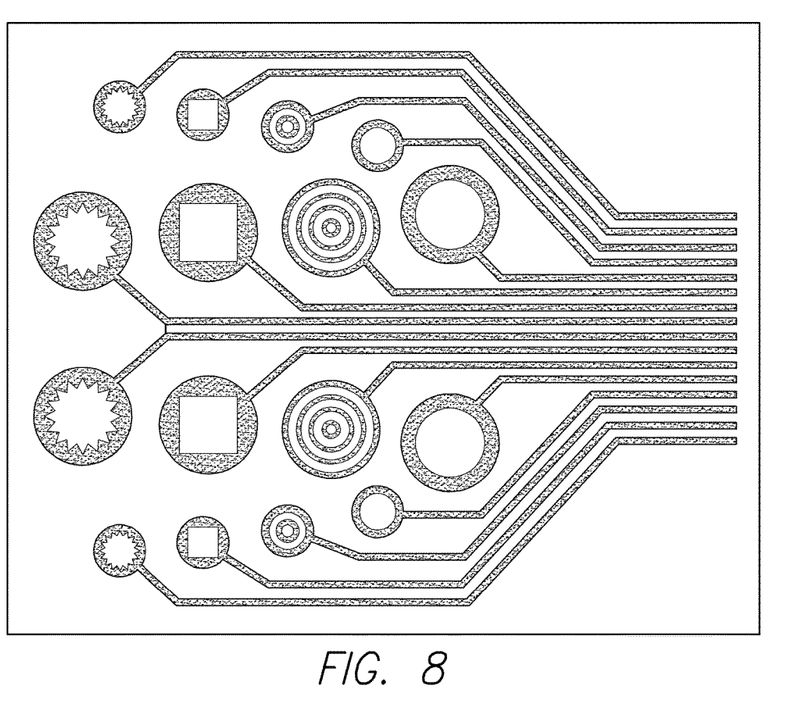
FIG. 8 depicts an electrode array with different shapes of fixtures.

FIG. 8 depicts an electrode array with different shapes of fixtures. Circle shapes, star shapes, square shapes and rings are shown in the electrode array. Each of the shapes contains overlapping edges and mesh grids. This presents a series of new electrode geometries that control charge transfer characteristics by the strategic use of edges and corners to concentrate current delivery. These designs are an improvement on conventional surface electrode designs which are typically circles.

The present invention will be further explained in detail by the following example.

Example

General Procedure

Platinum Plating Solution Preparation 0.3 g sodium dihydrogen phosphate ($NaH_2PO_4$) and 6.03 g disodium hydrogen phosphate ($Na_2HPO_4$) [Fluka] were dissolved in 100 ml deionized water, and stirred by magnetic stirring for 30 minutes. The concentrations for $NaH_2PO_4$ and $Na_2HPO_4$ were 25 mM and 425 mM. Then 0.5 g of Platinum chloride ($PtCl_4$) [Alfa Aesar] was added to the phosphate solution to form the platinum salt concentrations of 15 mM. The solution was then stirred for 30 minutes. Different concentrations of ($PtCl_4$) were used in the experiments and the range of Pt salt concentrations was from 3 to 30 mM. The pH of the solution was measured at 7.9. The color of the solution was amber. The solution was deaerated before the plating process by bubbling nitrogen through the solution.

Preparation of the Substrate

A thin-film platinum polyimide array was used for platinum plating. The array included 16 electrodes with 200 μm thin-film Pt disk as exposed electrode surface. All the electrodes in the array were shorted to common contact points for the plating. The Pt disk electrodes were first electrochemically cleaned by bubbling the surface with oxygen at +2.8V vs Ag/AgCl in 0.5 M $H_2SO_4$ for 10 sec. Then the surface was cleaned by bubbling with hydrogen at −1.2 V vs Ag/AgCl in 0.5 M $H_2SO_4$ for 15 sec to remove surface contaminations and polymer residues.

Electroplating Cell

A classical Pyrex glass three-electrode reaction cell was used for the electroplating. The reference electrode compartment was separated from the reaction compartment by a Vicor porous frit, in order to avoid the migration of concentrated KCl and AgCl from the inner filling solution of the reference electrode to the plating bath. The counter electrode was a platinized-platinum sheet of a real surface area equal to 1.8 $cm^2$.

A digital magnetic stirrer (Dataplate PMC720) was used to agitate the solution during plating. The solution temperatures were from 15° C. to 80° C. and were controlled by a VWR circulating water bath with a digital temperature controller (VWR 1147P).

The potential was controlled by using an EG&G PARC model 273 potentiostat-galvanostat and the response current, current density and charge were recorded by EG&G PARC M270 software. The charge/charge density and average plating current/current density were calculated by integrating the area under the plating current vs. time curve. The plating time was from 1 minute to 60 minutes.

Platinum Plating

A platinum polyimide electrode array having 16 electrodes (FIG. 14) having a diameter of 200 μm platinum disc on the array was cleaned electrochemically in 0.5 M $H_2SO_4$. The electrode array was placed in an electroplating cell containing a plating solution having a concentration of 15 mM platinum chloride in 0.025 M sodium dihydrogen phosphate and 0.425 M disodium hydrogen phosphate. The plating bath temperature was at 22° C. A constant voltage of −0.525 V vs Ag/AgCl reference electrode was applied on the electrode and terminated after 10 minutes. The electrode array was thoroughly rinsed in deionized water. The charge/charge density and average plating current/current density were calculated by integrating the area under the plating current vs. time curve. The current density was near linearly increased from initial 11.1 $A/cm^2$ to final 15.2 $A/cm^2$. The electrochemical capacitance of the electrode array with the surface coating of rough platinum was 1462 $\mu F/cm^2$, measured in a 10 mM phosphate buffered saline solution. The thin-film Pt disks only have an average capacitance of less than 20 $\mu F/cm^2$ before plating measured at the same condition. The optimal voltage drop across the electrodes for producing rough platinum was from −0.4 to −0.7 Volts vs. Ag/AgCl reference electrode. The plated platinum surface coating thickness is about 3.5 μm. The electrochemical active surface area increase is about 73 fold. The relation of surface area to the thickness of the platinum surface coating is 4.18 $F/cm^3$ [surface coating of rough platinum 1462 $\mu F/cm^2$ per thickness of the platinum coating of 3.5 μm.] The platinum surface coating adhesive strength was 55 mN.

Procedure

On a glass substrate, a 5 μm polyimide was spin coated on. A thin-layer Pt (~5000 A) is sputtered then coated with polyimide having a thickness of about 5 μm with openings ranged from 30 μm to 400 μm. On each sample, 16 such openings are exposed as electrode surfaces for plating. A photoresist mask is coated on these electrode openings with some holes patterned.

The electrode sample was electrochemically cleaned in 0.5 M sulphuric acid by applying a dc voltage to cause water hydrolysis. Then the sample was rinsed with DI water thoroughly.

150 ml glass beakers are used as the electroplating cell. A large surface area Pt sheet was used as a common electrode (anode). The reference electrode was an Ag/AgCl electrode (silver-silver chloride electrode).

About 100 ml of 18 mM Ammonium hexachloroplatinate in phosphate buffer solution was used to plating Pt.

Arrange the electrode in the test cell, so that the plating electrode (cathode) is in parallel with the common electrode (anode). The reference electrode is positioned beside the cathode. Add the plating solution with specified concentration. Turn on the magnetic stirrer. The solution agitation is controlled by a magnetic stirrer (VWR Thermolyne Cimarec 1). The typical plating temperature was about 24-26° C.

A voltage waveform (1 ms pulse width square wave) is generated by HP 33120A arbitrary waveform generator, which is converted to current signal through a FHC isolator. The pulse current is a square wave at 500 Hz with a 1 ms pulse width.

Apply this pulse current on the plating electrode vs anode. The electrode voltage vs Ag/AgCl reference electrode is monitored using an oscilloscope (Tektronix TDS3014B Oscilloscope). The current amplitude was adjusted so that the cathodic peak voltage reaches about −0.6V vs Ag/AgCl reference electrode. During plating, the electrode voltage tends to decrease with plating time. The current amplitude is frequently adjusted so that the electrode voltage is kept within −0.5 to −0.7 V range vs Ag/AgCl reference electrode. When specified plating time is reached, terminate the current pulse. Rinse the cathode in DI water thoroughly.

The photoresist mask was dissolved in solvent to leave electroplated Pt posts exposed on the thin film metal surface. The plated samples are profiled to measure the height of the plated posts. The plated posts have a height of 8 μm, ranging from 4 to 25 μm.

The gaps around the Pt posts were then filled with a layer of PDMS or polyimide. The final sample was examined under a microscope.

After plating, the current amplitudes are averaged for the whole plating time. It is found that the charge density increases exponentially with sample opening decrease. The smaller the sample openings, the higher the charge density required.

Accordingly, what has been shown is an improved flexible circuit with an electronics control unit attached thereto, which is suitable for implantation in living tissue and to transmit electrical impulses to the living tissue. Obviously, many modifications and variations of the present invention are possible in light of the above teachings. It is therefore to be understood that, within the scope of the appended claims, the invention may be practiced other than as specifically described.

What we claim:

1. A method of manufacturing an electrode with increased stability, comprising:
   a) providing a polymer base layer;
   b) depositing a metal layer on the polymer base layer, the metal layer forming a single electrode base;

c) applying polymer top layer covering the edges of the single electrode base;
d) applying photoresist layer on the single electrode base;
e) patterning the photoresist layer providing a plurality of openings through the photoresist layer to the single electrode base;
f) electroplating the openings with metal forming a plurality of protrusions on the single electrode base;
g) removing the photoresist layer leaving a plurality of spaces between the plurality of protrusions on the single electrode base; and
h) filling the plurality of spaces with a polymer cover layer, wherein the plurality of protrusions extend beyond the polymer cover layer;
wherein the plurality of protrusions separated by the polymer cover layer are electrically connected with the single electrode base extending under the polymer cover layer and forming part of the single electrode having an increase in electrode polymer cover layer edge length of the single electrode as compared with an electrode of the same size without the polymer cover layer in the spaces.

2. The method according to claim 1, wherein the metal comprises Pt, Ir, Au, Ru, Pd, IrO or alloys thereof and the polymer base layer comprises polyimide, silicone, peek or parylene, or mixtures thereof.

3. A method of manufacturing an electrode with increased stability, comprising:
a) providing a polymer base layer;
b) depositing a metal layer on the polymer base layer, the metal layer forming a single electrode base;
c) applying a polymer top layer on the metal layer, covering at least the edges of the single electrode base;
d) applying photoresist layer on the polymer layer;
e) patterning the photoresist layer providing a plurality of openings through the polymer layer to the single electrode base;
f) electroplating the openings with metal, forming a plurality of protrusions on the single electrode base extending beyond the polymer top layer; and
g) removing the photoresist layer
wherein the plurality of protrusions separated by the polymer top layer are electrically connected and common forming part of the single electrode having an increase in electrode polymer top layer edge length of the single electrode as compared with the electrode without the polymer top layer.

4. The method according to claim 3, wherein the metal comprises Pt, Ir, Au, Ru, Pd, IrO or alloys thereof and the polymer base layer comprises polyimide, silicone, peek or parylene, or mixtures thereof.

5. The method according to claim 1, wherein the increase in electrode polymer cover layer edge length is 100% or greater.

6. The method according to claim 1, wherein the increase in electrode polymer cover layer edge length is 120% or greater.

7. The method according to claim 3, wherein the increase in electrode polymer top layer edge length is 100% or greater.

8. The method according to claim 3, wherein the increase in electrode polymer top layer edge length is 120% or greater.

* * * * *